United States Patent
Vincent et al.

(10) Patent No.: US 7,238,165 B2
(45) Date of Patent: Jul. 3, 2007

(54) FLUID PUMP

(75) Inventors: Douglas Vincent, Pelham, NH (US); Matthew J. Murphy, Braintree, MA (US)

(73) Assignee: Design Mentor, Inc., Pelham, NH (US)

( * ) Notice: Subject to any disclaimer, the term of this patent is extended or adjusted under 35 U.S.C. 154(b) by 305 days.

(21) Appl. No.: 10/372,023

(22) Filed: Feb. 21, 2003

(65) Prior Publication Data

US 2004/0015042 A1    Jan. 22, 2004

Related U.S. Application Data

(60) Provisional application No. 60/358,547, filed on Feb. 21, 2002.

(51) Int. Cl.
*A61M 37/00* (2006.01)
*A61M 1/10* (2006.01)
*A61M 1/00* (2006.01)
*A61M 31/00* (2006.01)
*A61N 1/362* (2006.01)

(52) U.S. Cl. ............... 604/6.11; 604/6.1; 604/67; 422/44; 623/3.11; 623/3.19; 600/16; 417/437; 417/412

(58) Field of Classification Search .............. 604/4.01, 604/6.09, 6.1, 6.11, 65–67, 7–10, 6.13, 6.14; 210/645, 90; 422/44–48; 623/3.1, 3.16, 623/3.17, 3.11; 222/209; 417/65, 85, 86, 417/412, 426, 321, 375, 410.1, 413.1, 477.2; 600/16–17

See application file for complete search history.

(56) References Cited

U.S. PATENT DOCUMENTS 3,633,217 A    1/1972    Lance et al. .................. 3/1

(Continued)

FOREIGN PATENT DOCUMENTS

EP    0665713    8/2002

(Continued)

OTHER PUBLICATIONS

Anderson; Blood Pumps: Technologies and Markets in Transformation; 2001; pp. 406-410; Artificial Organs, vol. 25, No. 5.

(Continued)

*Primary Examiner*—Tatyana Zalukaeva
*Assistant Examiner*—Leslie R. Deak
(74) *Attorney, Agent, or Firm*—Bourque and Associates (57) ABSTRACT

A pumping system 10 provides a physiological pulsatile flow and includes controller 121, a pump drive head 50 coupled to a motor 12 and a fluid housing 52 having at least one port 60. The port 60 includes a ball valve retainer region 69, a valve seat 73, and an occluder ball 71 disposed in the ball valve retainer region 69. During operation, the motor 12 forces the fluid in and out the fluid housing 52 and causes the occluder ball 71 to move from a first position whereby the fluid cannot pass through the port 60, to a second position whereby the fluid moves annular to and generally around the occluder ball 71. This movement creates a slight flow reversal that "breaks up" any blood clots that may form. The pumping system may be used as part of a cardiopulmonary bypass system, a ventricular assist device (VAD) and/or a heart pump.

18 Claims, 8 Drawing Sheets

U.S. PATENT DOCUMENTS

| | | | | |
|---|---|---|---|---|
| 3,771,173 | A | | 11/1973 | Lamb, Jr. ........................... 3/1 |
| 3,771,899 | A | | 11/1973 | Brumfield .................... 415/90 |
| 3,842,440 | A | * | 10/1974 | Karlson ..................... 623/3.19 |
| 3,874,002 | A | | 1/1975 | Kurpanek .......................... 3/1 |
| 3,911,897 | A | | 10/1975 | Leachman, Jr. ................ 128/1 |
| 4,162,543 | A | * | 7/1979 | Shumakov et al. ......... 623/3.21 |
| 4,173,796 | A | | 11/1979 | Jarvik ............................ 3/1.7 |
| 4,222,127 | A | | 9/1980 | Donachy et al. ................ 3/1.7 |
| 4,293,961 | A | | 10/1981 | Rungo ............................ 3/1.7 |
| 4,541,787 | A | | 9/1985 | DeLong ..................... 417/417 |
| 4,648,877 | A | * | 3/1987 | Lundback .................. 623/3.17 |
| 4,662,358 | A | * | 5/1987 | Farrar et al. .................. 600/16 |
| 4,787,823 | A | * | 11/1988 | Hultman ..................... 417/45 |
| 4,965,864 | A | | 10/1990 | Roth et al. .................. 318/135 |
| 5,011,380 | A | | 4/1991 | Kovacs ....................... 417/413 |
| 5,064,353 | A | | 11/1991 | Tsukahara .................. 417/383 |
| 5,066,300 | A | | 11/1991 | Isaacson et al. ............... 623/3 |
| 5,089,016 | A | | 2/1992 | Millner et al. ................. 623/3 |
| 5,089,018 | A | | 2/1992 | Lapeyre et al. ................ 623/3 |
| 5,171,207 | A | | 12/1992 | Whalen ....................... 600/16 |
| 5,216,723 | A | | 6/1993 | Froeschle et al. ........... 381/201 |
| 5,266,265 | A | | 11/1993 | Raible ......................... 422/46 |
| 5,270,005 | A | | 12/1993 | Raible ......................... 422/46 |
| 5,300,015 | A | | 4/1994 | Runge ......................... 600/16 |
| 5,300,111 | A | | 4/1994 | Panton et al. ................... 623/3 |
| 5,411,706 | A | | 5/1995 | Hubbard et al. .............. 422/46 |
| 5,431,626 | A | | 7/1995 | Bryant et al. ................. 604/65 |
| 5,476,368 | A | * | 12/1995 | Rabenau et al. ............ 417/395 |
| 5,588,816 | A | * | 12/1996 | Abbott et al. ............... 417/479 |
| 5,676,651 | A | | 10/1997 | Larson, Jr. et al. ........... 604/33 |
| 5,743,845 | A | | 4/1998 | Runge ......................... 600/16 |
| 5,770,149 | A | | 6/1998 | Raible ......................... 422/46 |
| 5,785,686 | A | | 7/1998 | Runge ......................... 604/96 |
| 5,820,579 | A | | 10/1998 | Plotkin ........................... 604/5 |
| 5,823,930 | A | | 10/1998 | Runge et al. ................. 600/16 |
| 5,827,220 | A | | 10/1998 | Runge ......................... 604/49 |
| 5,916,191 | A | | 6/1999 | Plunkett et al. ................ 604/4 |
| 5,928,179 | A | | 7/1999 | Plotkin .......................... 604/4 |
| 5,984,960 | A | | 11/1999 | Vitale ............................ 623/3 |
| 6,123,724 | A | | 9/2000 | Denker ..................... 623/3.11 |
| 6,190,409 | B1 | | 2/2001 | Vitale ........................ 623/3.18 |
| 6,264,601 | B1 | | 7/2001 | Jassawalla et al. ........... 600/16 |
| 6,405,599 | B1 | | 6/2002 | Patt ............................. 73/779 |
| 6,428,747 | B1 | | 8/2002 | Dueri et al. ................... 422/46 |
| 6,443,922 | B1 | | 9/2002 | Roberts et al. ............ 604/4.01 |
| 6,532,964 | B2 | | 3/2003 | Aboul-Hosn et al. ....... 128/898 |
| 2002/0085952 | A1 | | 7/2002 | Ellingboe et al. ............. 422/45 |
| 2002/0087107 | A1 | | 7/2002 | Roberts et al. ............ 604/5.01 |
| 2002/0128587 | A1 | | 9/2002 | Aboul-Hosn et al. .......... 604/7 |
| 2002/0128597 | A1 | | 9/2002 | Grimes et al. ........... 604/96.01 |

FOREIGN PATENT DOCUMENTS

| | | |
|---|---|---|
| WO | WO 9406292 | 3/1994 |
| WO | WO 9740867 | 11/1997 |
| WO | WO 9949913 | 10/1999 |
| WO | WO 0072897 | 12/2000 |
| WO | WO 0143797 | 6/2001 |

OTHER PUBLICATIONS

Anstadt et al.; Pulsatile Versus Nonpulsatile Reperfusion Improves Cerebral Blood Flow After Cardiac Arrest; 1993; pp. 453-461; The Annals of Thoracic Surgery, vol. 56.

Bachmann et al.; Fluid Dynamics of a Pediatric Ventricular Assist Device; 2000; pp. 362-372; Artificial Organs, vol. 24, No. 5.

Borger et al.; Neuropsychologic Impairment After Coronary Bypass Surgery: Effect of Gaseous Microemboli During Perfusionist Interventions; Apr. 2001; pp. 743-749; The Journal of Thoracic and Cardiovascular Surgery, vol. 121, No. 4.

Burdick et al., National Impact of Pulsatile Perfusion On Cadaveric Kidney Transplantation; Dec. 27, 1997; pp. 1730-1733; Transplantation, vol. 64, No. 12.

Burgreen, et al.; Computational Fluid Dynamics as a Development Tool for Rotary Blood Pumps; 2001; pp. 336-340; Artificial Organs, vol. 25, No. 5.

Canivet, et al.; Plasma renin activity and urine $\beta_2$-microglobulin during and after cardiopulmonary bypass: pulsatile vs non-pulsatile perfusion; 1990; pp. 1079-1082; European Heart Journal, No. 11.

Chew et al.; Tissue Injury and the Inflammatory Response to Pediatric Cardiac Surgery with Cardiopulmonary Bypass; 2001; pp. 745-753; Anesthesiology, V. 94, No. 5.

Chow, et al.; The Relation Between Pump Flow Rate And Pulsatility On Cerebral Hemodynamics During Pediatric Cardiopulmonary Bypass; Oct. 1997; pp. 568-577; The Journal Of Thoracic and Cardiovascular Surgery, vol. 114, No. 4.

Degirmenci et al.; The Effect of Coronary Artery Bypass Surgery on Brain Perfusion; Apr. 1998; pp. 587-591; The Journal of Nuclear Medicine, vol. 39, No. 4.

Fiore, et al.; Development of a New Disposable Pulsatile Pump for Cardiopulmonary Bypass: Computational Fluid-Dynamic Design and In Vitro Tests; May 2002; pp. 260-267; American Society for Artificial Internal Organs (ASAIO) Journal.

Fumero, et al.; Clinical experience with a new pulsatile pump for infant and pediatric cardiopulmonary bypass; 1989; pp. 314-320; The International Journal of Artificial Organs, vol. 12.

Gaer, et al.; Effect of Cardiopulmonary Bypass on Gastrointestinal Perfusion and Function; 1994; pp. 371-375; Annual Meeting of The Society of Thoracic Surgeons, vol. 57.

Gage, et al.; Comparison of Static Versus Pulsatile Preservation of Matched-Paired Kidneys; 1997; pp. 3644-3645; Transplant Proceedings, 29.

Gerritsen, et al; Off-pump versus on-pump coronary artery bypass grafting: oxidative stress and renal function; 2001; pp. 923-9929; European Journal of Cardio-thoracic Surgery 20.

Grossi, et al.; Quantification of pulsatile flow during cardiopulmonary bypass to permit direct comparison of the effectiveness of various types of "pulsatile" and nonpulsatile flow; Sep. 1985; pp. 547-553; Surgery, vol. 98, No. 3.

Henze, et al.; Cerebral Dysfunction Following Extracorporeal Circulation for A Aortacoronary Bypass Surgery: No Differences in Neuropsychological Outcome After Pulsatile Versus Nonpulsatile Flow; 1990; pp. 65-68; Thoarac.cardiovasc. Surgn 38.

Inzoli, et al.; Influence of membrane oxygenators on the pulsatile flow in extracorporeal circuits: an experimental analysis; 1997; pp. 455-462; The International Journal of Artificial Organs, vol. 20, No. 8.

Jacobs, et al.; Alternations of Neuropsychological Function and Cerebral Glucose Metabolism After Cardiac Surgery Are Not Related Only To Intraoperative Microembolic Events; 1998; pp. 660-667; American Heart Association.

Jacobs, et al., Improved organ function during cardiac bypass with a roller pump modified to deliver pulsatile flow; Nov. 1969; pp. 703-712; Journal of Thoracic and Cardiovascular Surgery, vol. 58, No. 5.

Johnson, et al.; The Influence of Pulsatile Perfusion on the Vascular Properties of the Newborn Lamb Lung; 1992; pp. 349-353; International Pediatric Research Foundation, Inc., vol. 31, No. 4.

Kirkham; Recognition and Prevention of Neurological Complications in Pediatric Cardiac Surgery; 1998; pp. 331-340; Pediatric Cardiology, vol. 19, No. 4.

Leverett et al.; Red Blood Call Damage By Shear Stress; 1972; pp. 257-273; Biophysical Journal, vol. 12.

Liepsch, et al.; Pulsatile Flow Of Non-Newtonian Fluid In Distensible Models Of Human Arteries; 1984; pp. 571-586; Fifth International Congress of Biorheology And Third European Conference on Clinical Haemorhealogy—Symposium on Rheaology and Atherogenesis, vol. 21, No. 4.

Mathie, et al.; Hepatic Blood Flow During Cardiopulmonary Bypass Operations: The Effect Of Temperature and Pulsatility; Aug. 1997; pp. 292-293; The Journal of Thoracic and Cardiovascular Surgery, vol. 114, No. 2.

Mavroudis; To Pulse or Note To Pulse; Mar. 1978; pp. 259-271; The Annals of Thoracic Surgery, vol. 25. No. 3.

McMaster, et al; The Effect Of The Pulse On The Spread Of Substances Through Tissues; pp. 377-399.

Mori, et al.; Regional Blood Flow In the Liver, Pancreas, Kidney During Pulsatile and Nonpulsatile Perfusion Under Profound Hypothermia; Mar. 1988; pp. 219-227; Japanese Circulation Journal, vol. 52.

Mutch, et al; Biologically Variable Pulsation Improves Jugular Venous Oxygen Saturation During Rewarming; 2000; pp. 491-497; The Annals of Thoracic Surgery, vol. 69.

Nishida, et al; Clinical Evaluation of Pulsatile Flow Mode of Terumo Capiox Centrifugal Pump; 1997; pp. 821; Artificial Organs, vol. 21, No. 7.

Onoe, et al.; The effect of pulsatile perfusion on cerebral blood flow during profound hypothermia with total circulatory arrest; Jul. 1994; pp. 119-125; The Journal of Thoracic and Cardiovascular Surgery, vol. 108, No. 1.

Parolari, et al.; Adult cardiac Surgery outcomes: role of the pump type; 2000; pp. 575-582; European Journal of Cardio-thoracic Surgery 18.

Polyak et al.; The Influence Of Pulsatile Preservation Of Renal Transplantation In The 1990s; Jan. 27, 2000; pp. 249-258; Transplantation, vol. 69, No. 2.

Shepard, et al.; Energy Equivalent Pressure; Nov. 1996; pp. 730-740; Arch Surg—vol. 93.

Shepard, et al.; Relation of pulsatile flow to oxygen consumption and other variables during cardiopulmonary bypass; Nov. 1969; pp. 694-702; Journal of Thoracic and Cardiopulmonary Surgery, vol. 58, No. 5.

Shum-Tim, et al.; Evaluation of a Pulsatile Pediatric Ventricular Assist Device in an Acute Right Heart Failure Model; 1997; pp. 1374-1380; Annals of Thoracic Surgery, vol. 64.

Slogoff, et al.; Role of Perfusion Pressure and Flow in Major Organ Dysfunction After Cardiopulmonary Bypass; 1990; pp. 911-918; Annals of Thoracic Surgery, vol. 50.

Taggart, et al.; Is Cardiopulmonary Bypass Still The Case Of Cognitive Dysfunction After Cardiac Operations?; Sep. 1999; pp. 414-421; The Journal of Thoracic and Cardiopulmonary Surgery, vol. 118, No. 5.

Taylor; Pulsatile cardiopulmonary bypass; 1981; pp. 561-568; Journal of Cardiovascular Surgery, vol. 22.

Taylor, et al.; Comparative studies of pulsatile and nonpulsatile flow during cardiopulmonary bypass, I. Pulsatile system employed and its hematologic effects; Apr. 1978; pp. 569-573; The Journal of Thoracic and Cardiovascular Surgery, vol. 75, No. 4.

Taylor, et al.; Comparative studies of pulsatile and nonpulsatile flow during cardiopulmonary bypass, II. The effects on adrenal secretion of cortisol; Apr. 1978; pp. 574-578; The Journal of Thoracic and Cardiovascular Surgery, vol. 75, No. 4.

Taylor, et al.; Comparative studies of pulsatile and nonpulsatile flow during cardiopulmonary bypass, III. Response of anterior pituitary gland to thyrotropin-releasing hormone; Apr. 1978; pp. 579-584; The Journal of Thoracic and Cardiovascular Surgery, vol. 75, No. 4.

Taylor, et al.; Peripheral vascular resistance and angiotensin II levels during pulsatile and non-pulsatile cardiopulmonary bypass; 1979; pp. 594-598; Thorax, vol. 34.

Taylor, et al.; Comparative clinical study of pulsatile and non-pulsatile perfusion in 350 consecutive patients; 1982; pp. 324-330; Thorax, vol. 37.

Tranmer, et al.; Pulsatile versus Nonpulsatile Blood Flow in the Treatment of Acute Cerebral Ischemia; Nov. 1986; pp. 724-731; Neurosurgery, vol. 19, No. 5.

Ündar, et al.; Effects Of Pulsatile Versus Nonpulsatile Flow On Cerebral Hemodynamics During Pediatric Cardiopulmonary Bypass With Deep Hypothermic Circulatory Arrest; 2002; pp. 1-4; Proceedings—23rd Annual Conference—IEEE/EMBS Oct. 25-28, 2001, Istanbul, Turkey.

Ündar, et al.; Effects of Perfusion Mode on Regional and Global Organ Blood Flow in a Neonatal Piglet Model; 1999; pp. 1336-1343; Annals of Thoracic Surgery, vol. 68.

Ündar, et al.; Evaluation of a Physiologic Pulsatile Pump System for Neonate-Infant Cardiopulmonary Bypass Support; 1999; pp. 53-58; American Society for Artificial Internal Organs (ASAIO) Journal.

Ündar, et al.; Pulsatile and Nonpulsatile Flows Can Be Quantified in Terms of Energy Equivalent Pressure Cardiopulmonary Bypass for Direct Comparisons; 1999; pp. 610-614; American Society for Artificial Internal Organs (ASAIO) Journal.

Ündar, et al.; The Effects of Pulsatile Versus Nonpulsatile Perfusion on Blood Viscoelasticity Before and After Deep Hypothermic Circulatory Arrest in a Neonatal Piglet Model; 1999; pp. 717-721; Artificial Organs, vol. 23, No. 8.

Ündar, et al.; Comparison of six pediatric cardiopulmonary bypass pumps during pulsatile and nonpulsatile perfusion; Oct. 2001; pp. 827-829; The Journal of Thoracic and Cardiovascular Surgery, vol. 122, No. 4.

Ündar, et al.; The Type of Aortic Cannula and Membrane Oxygenator Affect the Pulsatile Waveform Morphology Produced by a Neonate-Infant Cardiopulmonary Bypass System In Vivo; 1998, pp. 681-686; Artificial Organs, vol. 22. No. 8.

Ündar, et al.; Defining Pulsatile Perfusion: Quantification in Terms of Energy Equivalent Pressure; 1999; pp. 712-716; Artificial Organs, vol. 23, No. 8.

Ündar, et al.; Testing neonate-infant membrane oxygenators with the University of Texas neonatal pulsatile cardiopulmonary bypass system in vitro; 1998; pp. 346-352; Perfusion, vol. 13.

Vingerhoets, et al.; Short-term and long-term neuropsychological consequences of cardiac surgery with extracorporeal circulation; 1997; pp. 424-431; European Journal of Cardio-thoracic Surgery 11.

Waldenberger, et al.; A new pneumatic pump for extracorporeal circulation: TPP (True Pulsatile Pump). Experimental and first clinical results; 1998; pp. 447-454; The International Journal of Artificial Organs, vol. 20, No. 8.

Wardle, et al.; Cerebral oxygenation during cardiopulmonary bypass; Jan. 1998; pp. 26-32 (web pages 1-12); Archives of Disease in Childhood, vol. 78.

Watanabe, et al.; Pulsatile Low-Flow Perfusion for Enhanced Cerebral Protection; 1993; pp. 1478-1481; The Annals of Thoracic Surgery, vol. 56.

Wright; What Is Pulsatile Flow?; May 1985, pp. 401-402; The Annals of Thoracic Surgery, vol. 39, No. 5.

Wright; Homodynamic Analysis Could Resolve the Pulsatile Blood Flow Controversy; 1994; pp. 1199-1204; The Annals of Thoracic Surgery, vol. 58.

Xiao, et al.; Development of an Affordable Diaphragmatic Pump Cardiopulmonary Bypass: An In Vivo Evaluation; 2000; pp. 915-918; Artificial Organs, vol. 24, No. 11.

Lee; et al.; Evaluation of Pulsatile and Nonpulsatile Flow In Capillaries of Goat Skeletal Muscle Using Intravital Microscopy; 1994; 316-327; Microvascular Research, vol. 48.

\* cited by examiner

FLUID PUMP

CROSS-REFERENCE TO RELATED APPLICATIONS

This application claims the benefit of U.S. Provisional Application No.: 60/358,547 filed on Feb. 21, 2002 and fully incorporated herein by reference.

TECHNICAL FIELD

The present invention relates to pumps and more particularly, relates to a fluid pump, particularly suited to sterile fluids, that uses an electromagnetic linear motor.

BACKGROUND INFORMATION

Fluid pumps have been used in the medical industry, for example, to pump blood and other types of sterile fluids. Some existing fluid pumps are driven pneumatically. Other existing fluid pumps use stepping motors or screw type motors. These existing fluid pumps are often expensive, unreliable, too noisy, can damage blood and blood products, and/or unable to accurately control the fluid flow. Proper control of the pump and the fluid flow is particularly important when the fluid pump is used, for example, in a ventricular assist device (VAD), to pump blood which is susceptible to clotting.

Accordingly, there is a need for a fluid pump driven by a reliable linear motor that is capable of accurately controlling the pumping. There is also a need for an inexpensive fluid pump that is capable of providing the desired flow of fluid, for example,. to prevent clotting in blood.

SUMMARY

In accordance with one aspect of the present invention, a pumping system is provided. The pumping system comprises at least one linear electromagnetic motor including a core defining an air gap, at least one coil wrapped around at least a portion of the core proximate the air gap, and a magnet member, comprised of one or more magnets, located in the air gap and movable in a linear direction. Additionally, one or more magnets can be stationary and the wire coil can move through the air gap. At least one pump drive head is coupled to the moving member such that the pump drive head is movable in the linear direction. The pumping system further comprises at least one fluid housing defining a fluid chamber for containing a fluid. The fluid housing has a movable wall and one or more ports. The pump drive head contacts and moves the flexible membrane to drive the fluid through the port(s).

According to another aspect of the present invention, a fluid pump is provided. The fluid pump comprises a fluid housing defining a fluid chamber for containing a fluid. Inlet and outlet ports extend from the fluid housing and include or are coupled to valves, for example passive valves such ball valves, which allow fluid to flow in only one direction through the inlet and outlet ports. The fluid pump preferably includes a flexible membrane with a pump drive head molded therein.

According to a further aspect of the present invention, the fluid pump having the valves, as defined above, can be used in the pumping system with the linear motor establishing a physiologically pulsatile flow of fluid.

BRIEF DESCRIPTION OF THE DRAWINGS

These and other features and advantages of the present invention will be better understood by reading the following detailed description, taken together with the drawings wherein.

DETAILED DESCRIPTION OF THE PREFERRED EMBODIMENTS

Figure 1:
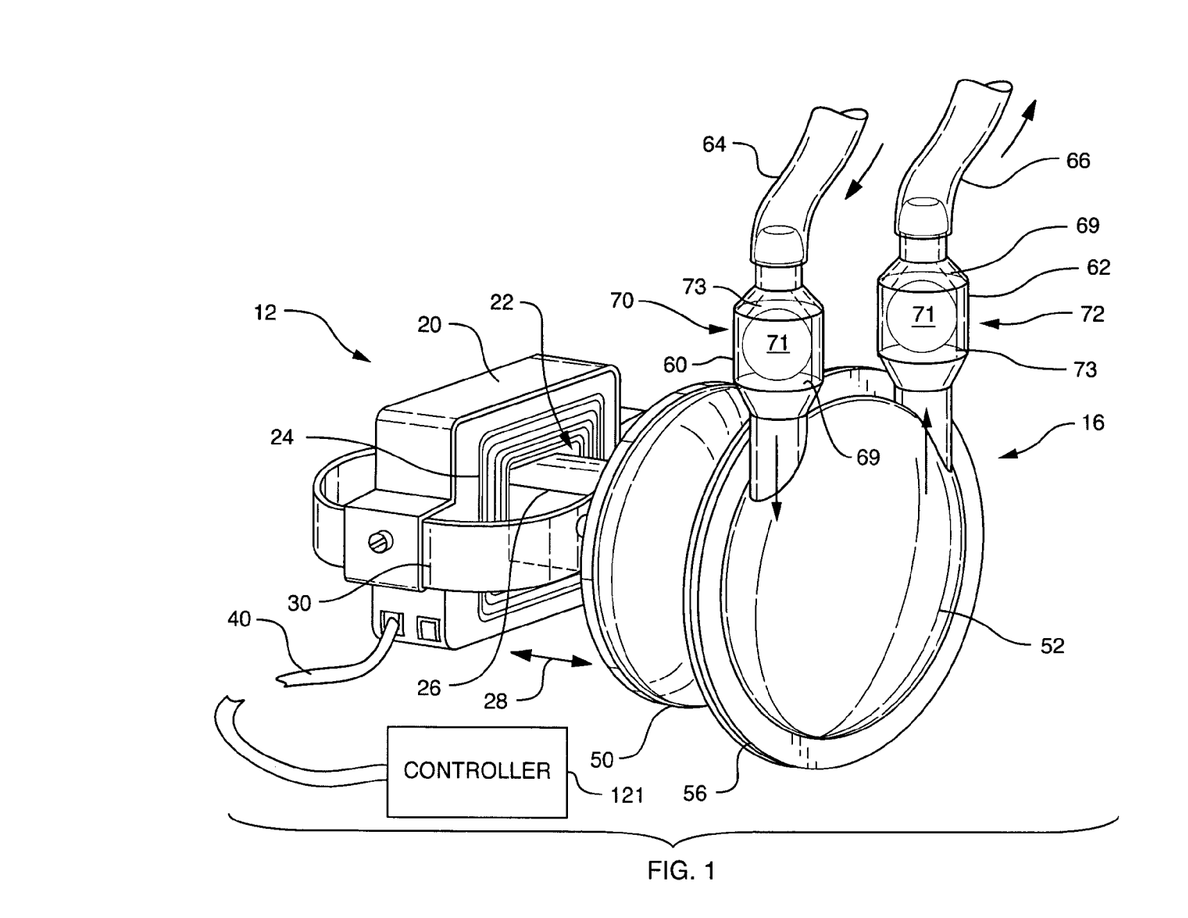
FIG. 1 is a schematic perspective view of a linear motor pumping system, according to one embodiment of the present invention.
Figure 2:
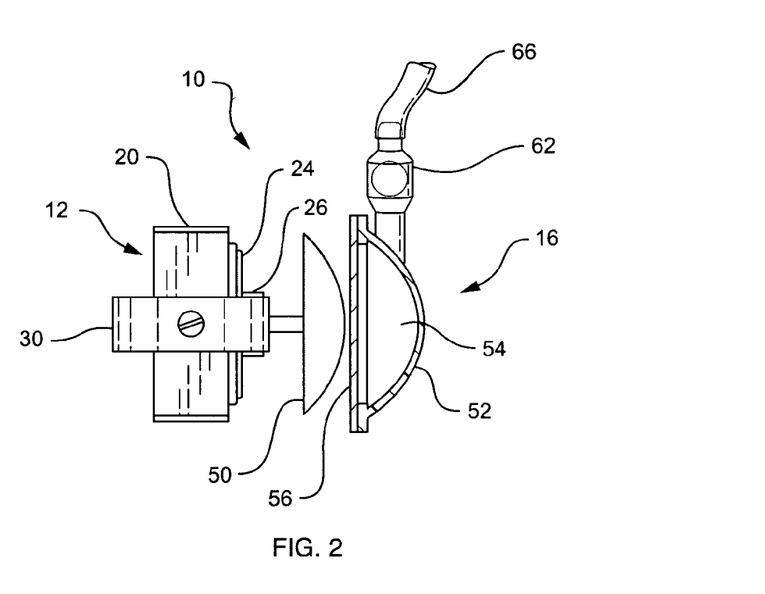
FIG. 2 is a partially cross-sectional side view of the linear motor pumping system shown in FIG. 1.

A linear motor fluid pumping system 10, FIGS. 1 and 2, according to one aspect of the present invention, is used to pump a fluid such as a liquid or a gas. The pumping system in accordance with the present invention is particularly well suited to pumping sterile fluids such as blood. The fluid pumping system 10 is capable of providing a consistent and controlled fluid flow and maintaining the fluid in a sterile environment. Thus, the fluid pumping system 10 is ideally suited for pumping sterile fluids in medical applications, for example, to pump blood in a ventricular assist device (VAD), as will be described in greater detail below. The fluid pumping system 10 can be used, however, to pump many other types of fluids in other applications.

The linear motor fluid pumping system 10 includes a linear motor 12 and a pump 16. The linear motor 12 is preferably a linear electromagnetic motor, such as the type disclosed in greater detail in U.S. Pat. No. 5,216,723, which is fully incorporated herein by reference. This linear motor 12 preferably provides relatively quiet, high torque, low speed linear motion. The linear motor 12 includes a core 20 defining an air gap 22. One or more coils 24 are wrapped around a portion of the core 20 proximate the air gap 22. A magnet member 26 is positioned in the air gap 22 and is movable in a linear direction as indicated generally by arrow 28.

A magnet member support 30 is preferably coupled between the magnet member 26 and the core 20. The magnet member support 30 is flexible and supports the magnet member 26 in the air gap 22 while allowing linear movement of the magnet member 26. The magnet member support 30 preferably includes a linear bearing or other similar guidance system. A power cord 40 is connected to the core 20 to provide an electrical current to the coil(s) 24 for driving the linear motor 12, as will be described in greater detail below.

Although the exemplary embodiment shows one configuration for the linear motor 12, other configurations, as described for example in U.S. Pat. No. 5,216,723 and incorporated herein by reference, are also within the scope of the present invention.

In one embodiment, a pump drive head 50 is coupled to the magnet member 26. The pump head is mechanically coupled to the moving magnet, such that the magnet can apply a force to the pump head in two directions, producing alternating pressure and vacuum in the pump chamber. The magnet member 26 thereby moves the pump drive head 50 in the linear direction shown generally by arrow 28, to directly engage the pump 16. Although this embodiment shows the pump drive head 50 having a dome shape, other shapes and configurations are within the scope of the present invention.

The pump 16 includes a fluid housing 52 defining a fluid chamber 54 containing the fluid to be pumped. The fluid housing 52 preferably includes a movable wall 56 on at least one side. The pump drive head 50 contacts and moves the movable wall 56 to contract and/or expand the fluid chamber 54, thereby forcing the fluid out of and/or drawing the fluid into the fluid chamber 54.

In one preferred embodiment, the housing 52 is made of a plastic material and the movable wall 56 is a flexible membrane made of an elastomer. By using the flexible membrane as the movable wall 56, the movable wall 56 returns to its original position when the pump drive head 50 retracts. Although the exemplary embodiment shows a generally dome-shaped housing 52, other shapes are within the scope of the present invention.

One or more ports 60, 62 extend from the fluid housing 52 to allow the fluid to pass into and/or out of the fluid housing 52. In one embodiment, a separate inlet port 60 and outlet port 62 extend from the fluid housing 52. An inlet tube 64 and an outlet tube 66 are coupled to the respective inlet port 60 and outlet port 62 to direct the fluid to the desired location, as will be described in greater detail below.

The inlet port 60 and outlet port 62 preferably include check valves to allow the fluid to flow in only one direction through the ports 60, 62. According to one preferred embodiment, the ports 60, 62 include ball valves 70, 72. The ball valve 70 allows the fluid to flow only into the fluid housing 52 and the ball valve 72 allows the fluid to flow only out of the housing 52. Alternatively, the ports 60, 62 may contain any other valve designs known to those skilled in the art such as, but not limited to, active and passive valves, for example, gate valves, pinch valves, magnetic valves, bi-leaflet valves, butterfly valves, solenoids, or the like to control or regulate the flow in and out of ports 60, 62 and fluid housing 52. Further, the ports 60 may be sized (length and/or volume) to achieve a desired amount of pulsatile flow.

One preferred embodiment of the ball valves 70, 72 includes three molded parts including a valve retainer region 69, a valve seat 73 and an occluder ball 71. When there is a positive pressure differential in the direction of flow, the occluder ball 71 is forced against the valve retainer 69, and flow is allowed to move annular to and generally around the occluder ball 71. When this pressure differential is reversed, the occluder ball 71 is forced against the valve seat 73 and flow is stopped, but not before causing some "reversal" in the flow of the fluid being pumped and thereby establishing a "pulsatile" fluid flow which is analogous to the normal physiological flow created by a beating heart. The use of the ball valves 70, 72 allows a substantially continuous, one-way pulsatile flow of fluid through the pump 16. The amount of "reversal" can be adjusted by varying the distance between the valve retainer 69 and the valve seat 73 which the occluder ball 71 travels and/or the volume of the ports 60, 62.

When used to pump blood, this substantially continuous physiologically pulsatile flow avoids clotting caused by low blood flow and thus lowers the risk of thrombosis and reduces the need for anti-coagulation medication. Further, it has been found that the pulsatile flow provided by the present invention actually causes a slight "reversal" in the flow of the fluid. This reversal of the fluid flow serves to "break up" boundary layers within the blood, improving circulation and preventing the formation of any blood clots that may form in those areas where such formation is common. Peak flow pressures open the smallest capillaries resulting in improved end organ perfusion. Physiologically pulsatile flow provided by the pump mimics the natural physiologically pulsatile flow generated by a normal human heart, which is understood to be better.

When current is applied to the linear motor 12, the magnet member 26 moves the drive head 50 against the movable wall 56 of the fluid housing 52. The movement of the movable wall 56 causes fluid to be pumped to and/or from the fluid chamber 54. Because the linear motor 12 is directly coupled to the fluid pump 16 without unnecessary mechanical linkages, there is a direct correlation between the current applied to the linear motor 12 and the fluid pressure. Varying the current applied to the linear motor 12 varies the stroke rate and force of the magnet member 26. Thus, the flow rate and pressure of the fluid medium can be dynamically controlled by simply controlling the electrical current provided to the linear motor 12. In other words, the flow and pressure can be varied during the stroke.

Other advantages of the linear motor fluid pumping system 10 include the ability to reliably determine the force applied by the linear motor, the pressure or vacuum drawn by the pump, and the position of the movable wall 56. Ultrasonic flow transducers can be used to measure the pressure and flow into and/or out of the fluid pump 16.

In one application, the linear motor 12 is driven, for example, with a sine wave having a frequency of about 1 Hz. The sinusoidal current results in the consistent reciprocating motion of the magnet member 26. The sine wave can be generated, for example, using a function generator (not shown).

The linear motor pumping system 10 can also provide a programmable flow profile. The force generated by the motor, and therefore the pressure generated within the pump, is directly related to the applied current. If a specific pressure waveform is required for a given application, it can be directly produced by generating a specific current waveform from a source controlling the current such as a microprocessor and/or a programmable function generator.

Figure 3:
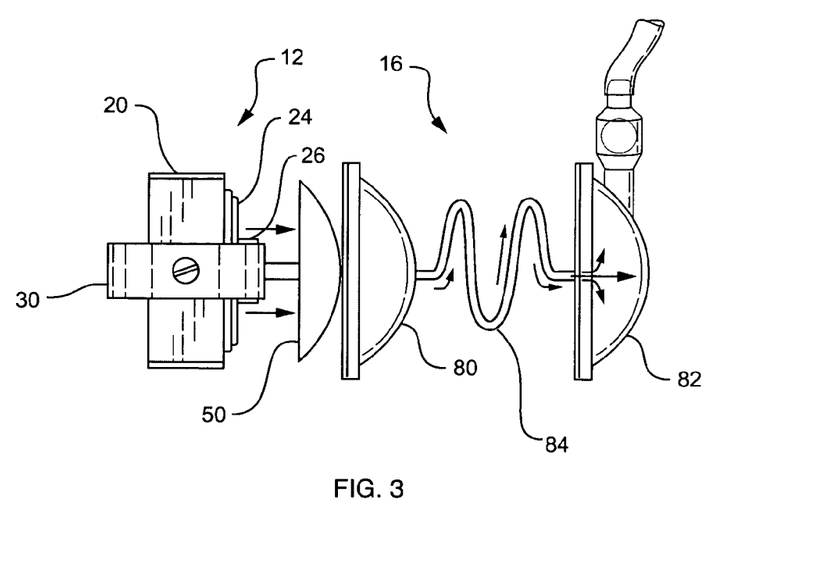
FIG. 3 is a schematic side view of a linear motor pumping system, according to another embodiment of the present invention.

An alternative embodiment of the fluid pump 16', FIG. 3, includes a first fluid housing 80 coupled to a second fluid housing 82 by way of a tube or air umbilical 84 containing a fluid. The first fluid housing 80 defines a fluid chamber containing an actuation fluid (e.g., air) and includes a movable wall similar to the fluid housing 52. The second fluid housing 82 defines a fluid chamber containing the fluid being pumped (e.g., blood) and includes inlet and outlet ports similar to the fluid housing 52.

When the pump drive head 50 engages the movable wall of the first fluid housing 80, the actuation fluid is forced out of the first housing 80 and through the tube 84. The actuation fluid causes the second fluid housing 82 to force the fluid through the outlet port. This embodiment allows the linear motor 12 and first fluid housing 80 to be located in a remote location (e.g., in a console) while the second fluid housing 82 is located proximate a patient.

Figure 4:
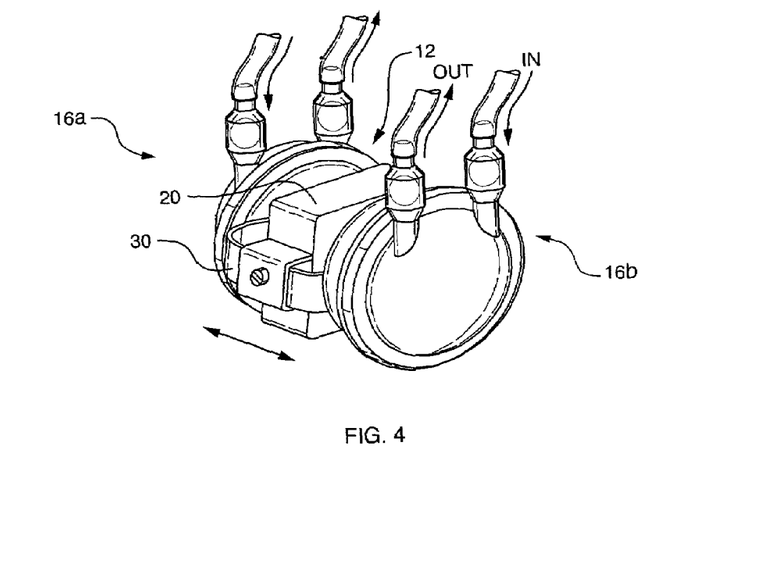
FIG. 4 is a schematic perspective view of a linear motor pumping system, according to a further embodiment of the present invention.
Figure 5:
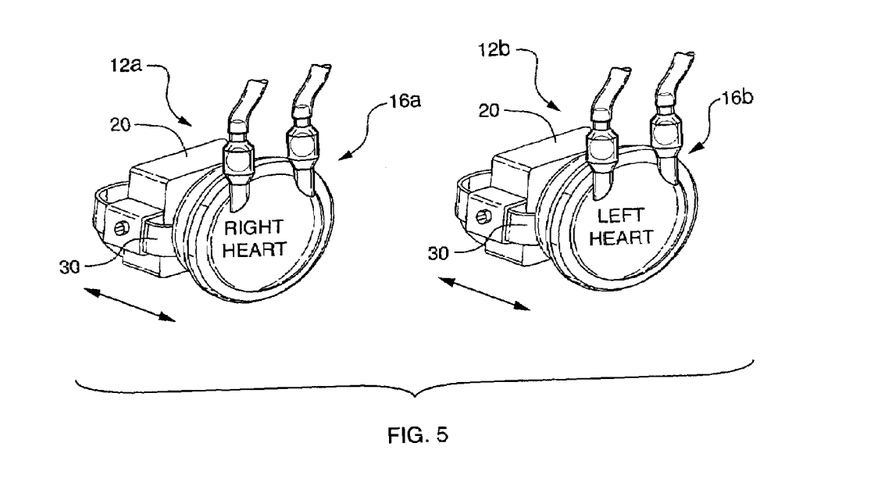
FIG. 5 is a schematic perspective view of a linear motor pumping system, according to yet another embodiment of the present invention.

According to further embodiments shown in FIGS. 4 and 5, two pumps 16*a*, 16*b* are used in the linear motor fluid pumping system. The two pumps 16*a*, 16*b* can be mounted on opposite sides of a single linear motor 12, as shown in FIG. 4, for example, to create a biventricular assist device (BiVAD). Reciprocating movement of the linear motor causes reciprocating movement in the actuator chambers which alternates vacuum and pressure to maintain a single direction of flow of the fluid.

The two pumps 16*a*, 16*b* can also be used with two separate linear motors 12*a*, 12*b*, as shown in FIG. 5, for example, to create a biventricular assist device (BiVAD). Although both of these embodiments show concepts of making a BiVAD, the embodiment in FIG. 4 shows the two pumps 16*a*/16*b* coupled with each other through one linear motor, while in FIG. 5, they are decoupled and require two motors.

Figure 6:
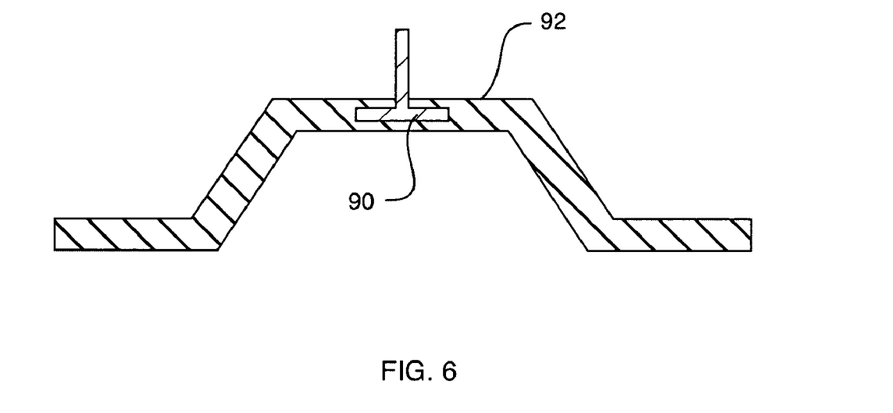
FIG. 6 is a cross-sectional view of a flexible wall used in a fluid pump, according to one embodiment of the present invention.
Figure 7:
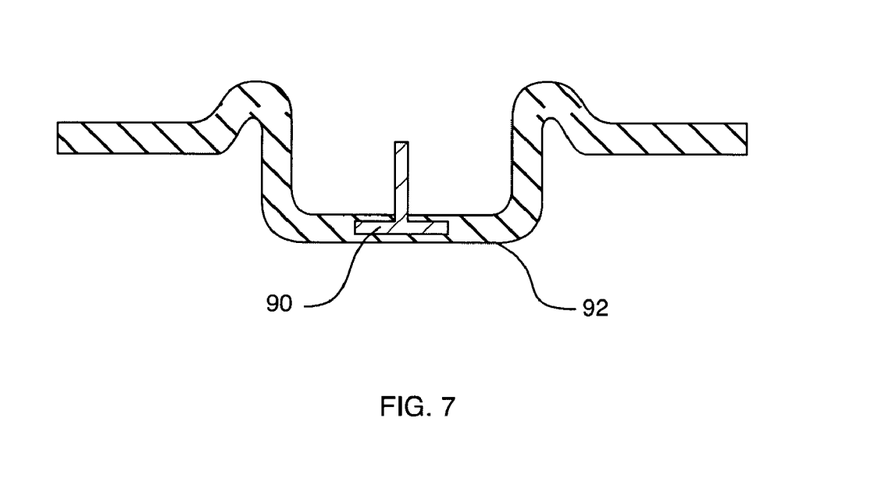
FIG. 7 is a cross-sectional view of the flexible wall shown in FIG. 6 in a compressed position.

According to one preferred embodiment, the pump drive head 90, FIGS. 6 and 7, is molded within the movable wall 92 of the pump 16. This embodiment provides direct coupling to the magnet member of the linear motor (not shown) such that the pump drive head 90 can both push and pull the movable wall 92 in order to drive fluids. The pushing and pulling action of the pump drive head 90 moves the moveable wall 92 between an outward or expanded position (FIG. 6) and an inward or compressed position (FIG. 7). This facilitates the fluid flow back into the fluid housing 52 through the inlet port 60. Although the exemplary embodiment shows the movable wall 92 as a flexible membrane having the pump drive head 90 molded therein, other forms of movable walls are also within the scope of the present invention. By molding the pump drive head within the movable wall 92, the linear motor can accelerate the movable wall 92 very quickly (i.e., much more quickly than a centrifugal pump, for example, can accelerate), thus the pump 16 is capable of generating complex flow and pressure dynamics or patterns as will be described in greater detail hereinbelow.

Figure 8:
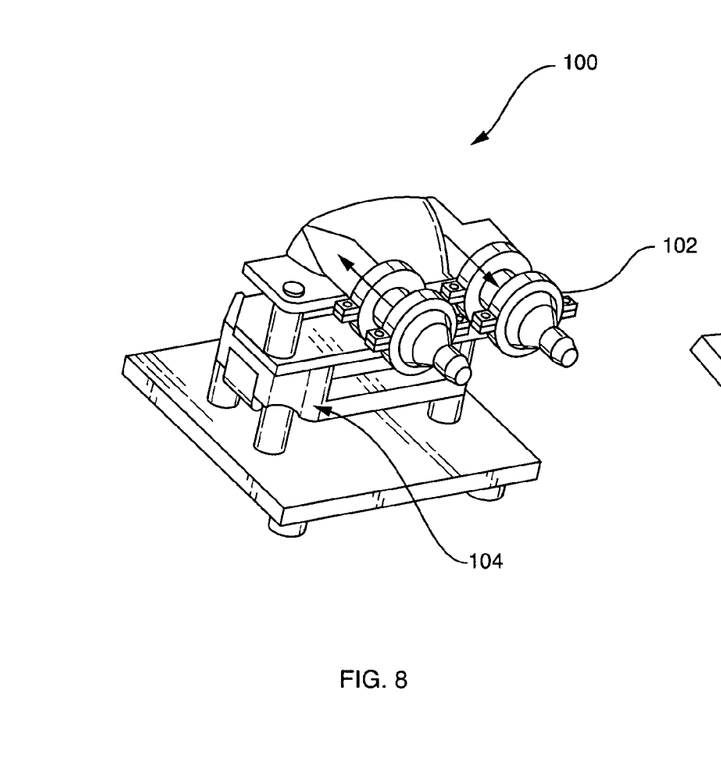
FIG. 8 is a perspective view of a blood pump, according to one embodiment of the present invention.
Figure 9:
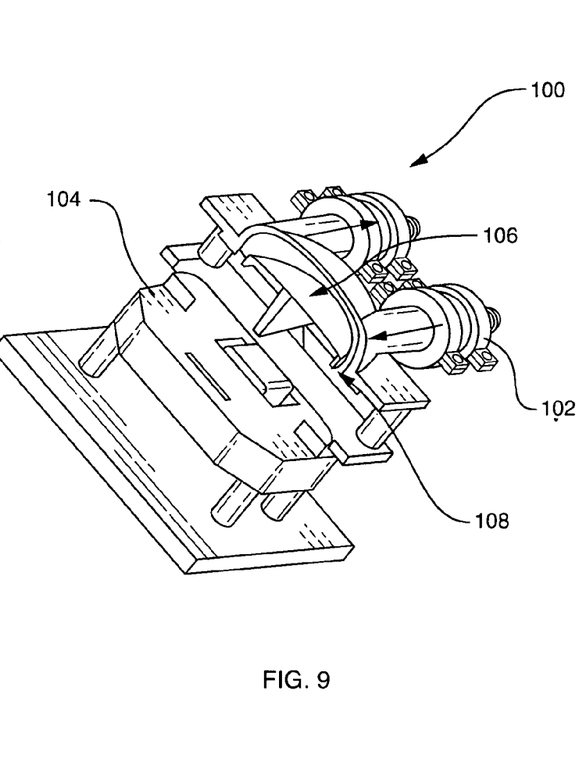
FIG. 9 is a partially cross-sectional view of the blood pump shown in FIG. 8.

One embodiment of a blood pump 100 used in a VAD (ventricular assist device), according to the present invention, is shown in greater detail in FIGS. 8 and 9. The blood pump 100 includes a ball valve assembly 102, a linear motor 104, a blood chamber 106, and a drive head or membrane pusher 108. The volume of the blood chamber 106 and the volume of fluid moved by the stroke of the pusher 108 will depend upon the patient. For example, a 50 cc chamber may be used for a child or neonate, with a 35 cc stroke for the child, and a 10–15 cc stroke for the neonate; whereas an 80 cc stroke and 120 cc chamber may be used for an adult. The electromechanical components are preferably outside of the fluid compartment making the issue of upkeep, cleaning and sterilizing the unit easier and less difficult.

According to various configurations, the blood pump 100 can provide two-chamber continuous flow with proper valve sequencing or can provide pulsatile flow. If two pumps are used in parallel, and they are controlled 180° out of phase, the output is a near constant flow. No active valving sequence would be required, again only the control and sequencing of the pump motors.

Figure 10:
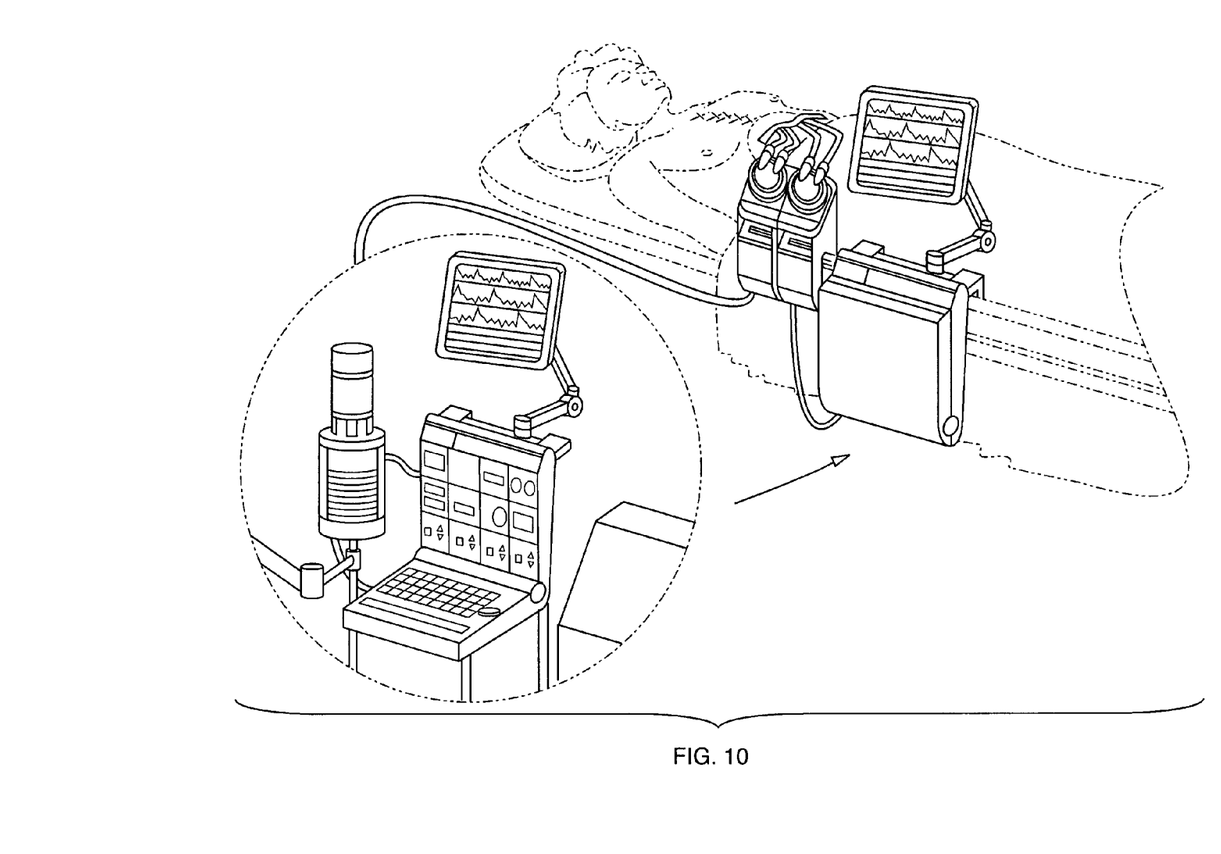
FIG. 10 is a schematic perspective view of a blood pump used with a patient, according to one embodiment of the present invention.

FIG. 10 shows the linear motor pumping system in a VAD used with a patient. In this example, the current to the linear motor (not shown) can be controlled to provide pumping consistent with the desired heart rate (e.g., 70 beats and 6 liters per minute for an adult).

Figure 11:
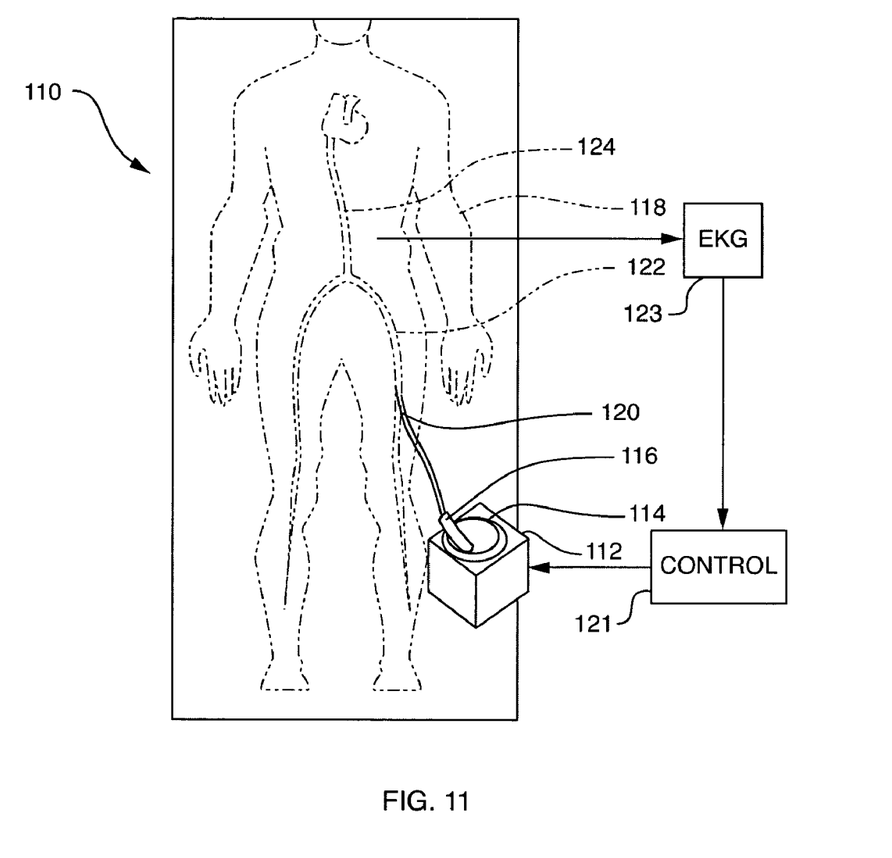
FIG. 11 is a schematic perspective view of a minimally invasive extracorporeal ventricular assist device used with a patient, according to another embodiment of the present invention.

In an alternative method of controlling the VAD, a controller 121, FIG. 11, having a microprocessor running software carrying out a control algorithm or an equivalent analog circuit prompts a user to input a diastolic pressure, a systolic pressure, and a stroke volume. Using these inputs, the controller 121 then applies a predetermined diastolic current to the motor during pump diastole to maintain the desired diastolic pressure. After this position is reached, the controller 121 will apply a predetermined systolic current to the motor to maintain the systolic pressure. The systolic current will apply a relative pumping pressure to the chamber 114 forcing blood into the patient's system 122. Instead of applying the diastolic and systolic currents for a specified time, the controller 121 may apply the currents until a predetermined plunger position (stroke volume) is reached. The time for each current will be variable, and dependent upon the pump preload (atrial pressure) and afterload (arterial pressure) respectively.

Thus, the controller 121 is capable of generating a physiological pulsatile flow as described above which mimics the normal flow generated by a beating heart. However, the controller 121 is also capable of generating any sort of pressure or flow dynamic or pattern by varying the current waveform and plunger stroke (volume) of the pump. As a result, the controller 121 is capable of generating arbitrary, programmable, or super-physiological waveforms wherein a higher (or lower) frequency waveform is generated in addition to, or over, the standard physiological waveform.

While the controller 121 is capable of generating these complex waveforms, the pump 16 of the pumping system 10 must also be capable of responding quickly enough to actually generate the desired flow patterns. The use of the linear motor 12, in combination with the pump drive head 50 molded into the movable wall 92 of the fluid housing 52 described hereinabove, allows the pump 16 to respond or accelerate quickly enough to generate the desired flow dynamics or patterns created by the controller 121. The controller 121 may also be combined, however, with any other pumping system capable of generating the desired flow dynamics or patterns.

When any pumping system is being used to support both the left and right ventricles, such as with a BiVAD or artificial heart, the two pumps must remain in balance with each other. This balance does not necessarily translate to equivalent flow rates. Instead, it should correlate to equivalent atrial pressures. Since the controller in the present invention is sensitive to atrial pressures, the pumps will adjust as atrial pressure change, allowing for the left and right atrial pressures to be maintained.

According to another embodiment, the present invention includes a minimally invasive extracorporeal VAD system 110, FIG. 11, for emergency cardiac support that provides a physiological pulsatile flow. The minimally invasive extracorporeal VAD system 110 includes a pump 112, preferably a moving magnet linear motor as described hereinabove, having a fluid chamber 114 and a single valveless port 116. The pump 112 is connected to the patient 118 using a percutaneous cannula 120 to the femoral artery 122. The timing of the pump 112 may be controlled by reading the EKG 123 of the patient 118 and providing feedback control of the pump 112 in response to the EKG values to the controller 121.

During native heart systole, the pump 112 fills fluid chamber 114. This filling applies a slight vacuum to the patient's arterial system 124, decreasing afterload and increasing cardiac output. During native heart diastole, the pump 112 empties fluid chamber 114, increasing the pressure of the patient's 112 arterial system 124. By increasing cardiac output and the pressure of arterial system 124, sufficient cardiac support is provided to stabilize the patient 118 and prepare the patient 118 for proper intervention, surgery or otherwise.

Figure 12:
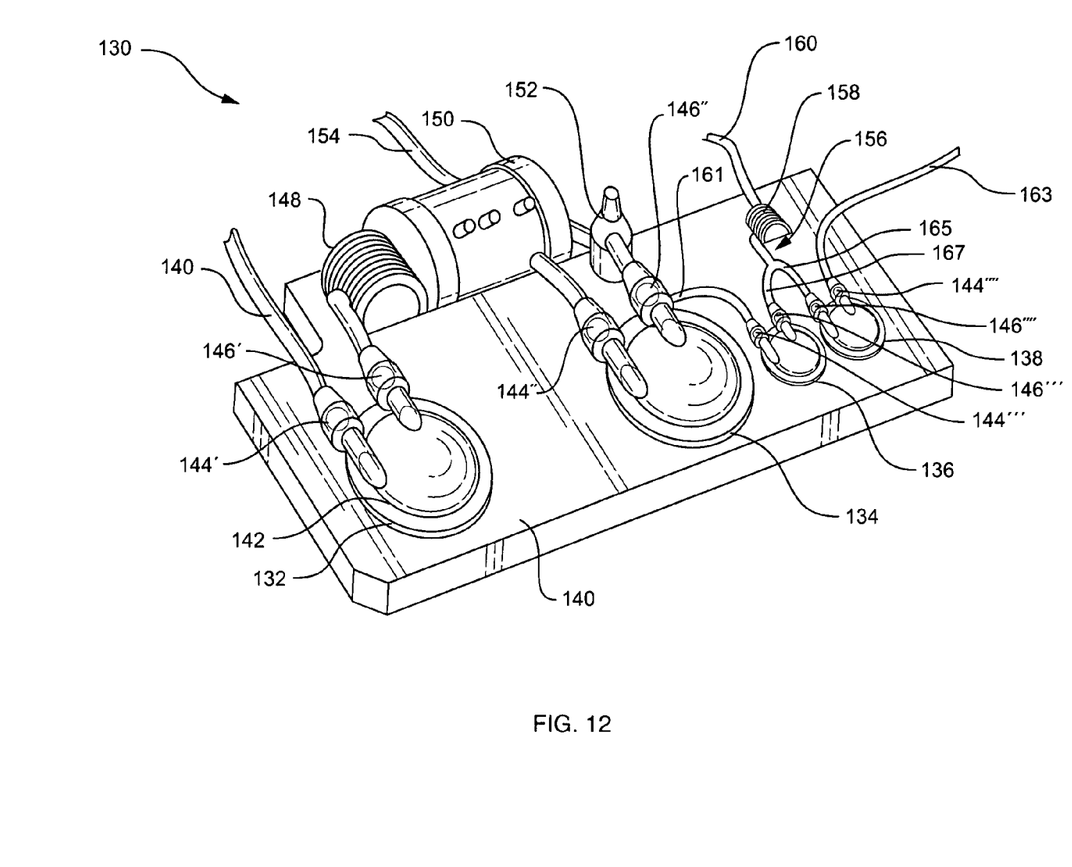
FIG. 12 is a schematic perspective view of an integrated cardiopulmonary bypass system, according to yet another embodiment of the present invention.

In yet another embodiment, the present invention includes an integrated cardiopulmonary bypass (CPB) system 130, FIG. 12 having four pumps 132, 134, 136, 138 which are preferably mounted to a support surface 140. The pumps 132, 134, 136, 138 may include any pump known to those skilled in the art, but preferably include a pump having a linear motor and an inlet and outlet port 144, 146 having the ball valve design disclosed herein.

The integrated cardiopulmonary bypass (CPB) system 130 is setup similar to a conventional CPB. Cannulation can be made in the traditional manner (not shown). Venous blood is preferably drained by gravity into a venous reservoir in a traditional manner (not shown). The venous reservoir monitors the volume and alarms if it is too low or too high. Blood is pulled from the venous reservoir through tube 140 by applying a vacuum to the proximal pump chamber 142 using the motor and the pump head (not shown). When pressure is applied to the proximal pump chamber 142, blood is forced out the outlet port 146' through a heat exchanger 148 and oxygenator 150. The heat exchanger 148 and oxygenator 150 are preferably connected to a temperature controlled water bath (not shown) and oxygen source (not shown), respectively, in the traditional manner. From the oxygenator 150, blood is pulled into the distal pump 134 through inlet port 144" in the same manner described hereinabove. When pressure is applied to the distal pump 134, blood is forced out the outlet port 146", through an arterial filter 152 and returned to the patient's arterial system through tube 154.

A portion of the arterial blood is shunted over to the cardioplegia blood pump 136 through tubes 161, 167 and ports 144''', 146''' and is then preferably mixed at junction 156 with a cardioplegia solution. The cardioplegia solution is metered by cardioplegia pump 138 and is drawn from a reservoir (not shown) through tubes 163, 165 and ports 144'''', 146'''' to junction 156. The blood and cardioplegia are then temperature controlled at the cardioplegia heat exchanger 158 and are pumped to the patient's myocardium through tube 160 to provide myocardial protection.

The proximal and distal pumps 132, 134 can be coupled so that they are always operating 180° out of phase. This will allow for filling of the distal pump 134 while the proximal pump 132 is emptying. That way, no compliance is required between the two. The proximal pump 132 can be run at low pressure since it is only pushing through the oxygenator 150 and heat exchanger 148, increasing the efficiency. The distal pump 134 preferably operates at a higher pressure, with the waveform programmed as such to deliver physiological pulsatile flow to the patient in any manner described herein without passing through the oxygenator 150 or heat exchanger 148 which could dampen the pulse. The cardioplegia pumps 136, 138 can be set to provide precise pressure to the antegrate or retrograde cardioplegia cannulae. As described hereinabove, the use of the ports 144, 146 having the ball valve configuration described above results in a slight "reversal" in the flow of the blood (fluids). This reversal of the fluid flow serves to "break up" boundary layers within the blood, improving circulation and preventing the formation of any blood clots that may form in those areas where such formation is common.

Other embodiments of the linear motor pumping system are also within the scope of the present invention. These other embodiments include, but are not limited to, using the linear motor 12 to drive the reciprocating piston in an IV pump, using the linear motor 12 to drive a syringe pump (e.g., for anesthesia or insulin delivery), using the linear motor 12 in a dialysis machine, and using the linear motor 12 in other sterile fluid pumping applications, such as laparascopic, cardiothoracic, cardiopulmonary by-pass and arthroscopic surgery.

The linear motor 12 can also be used for valving. The linear motor can be used to make active valves by using the motor to selectively occlude or open a fluid pathway. This fluid pathway could be a tube or a combination of a rigid and flexible component.

Modifications and substitutions by one of ordinary skill in the art are considered to be within the scope of the present invention, which is not to be limited except by the following claims.

The invention claimed is:

1. A pump for pumping a fluid comprising:
   at least one linear electromagnetic motor;
   at least one pump drive head, coupled to said linear electromagnetic motor, said pump drive head configured for movement in a linear direction;
   at least one fluid housing, responsive to said linear movement of said at least one pump drive head, and defining a deformable fluid chamber configured to contain a fluid, said fluid housing including a first and at least a second port, wherein said first port is configured to allow said fluid to flow substantially into said deformable fluid chamber and said second port is configured to allow said fluid to flow substantially out of said deformable fluid chamber, wherein said pump drive head is configured to deform said deformable fluid chamber causing a pressure differential within said deformable fluid chamber thus changing the volume of said deformable fluid chamber and forcing said fluid in or out said deformable fluid chamber through said first and second ports respectively; and
   a controller, coupled to said at least one linear motor, and configured to apply an energizing current to said linear electromagnetic motor in a predetermined waveform based upon a maximum positive energizing current value (systole) setting established in said controller, a maximum negative energizing current value (diastole) setting established in said controller, a cycle rate setting established in said controller, and the ratio of maximum positive to maximum negative energizing current value established in said controller such that said controller is configured to cause a maximum volume of fluid for a given pressure at a predetermined time and target pressure to be displaced within said fluid chamber.

2. The pump as claimed in claim 1 wherein said linear electromagnetic motor includes:
   a core defining an air gap;

at least one coil disposed around at least a portion of said core proximate said air gap; and a magnet member located in said air gap and movable in said linear direction.

3. The pump as claimed in claim 2 wherein said pump drive head is coupled to said magnet member.

4. The pump as claimed in claim 1 wherein
said fluid includes blood, and wherein said pump is configured to pump said blood from a venous reservoir coupled to said first port into said outlet port of said first pump and into a patient's arterial system.

5. The pump as claimed in claim 1 wherein said pump includes a first and a second fluid housing and a first and a second pump drive head coupled to a first and a second end of said linear electromagnetic motor respectively such that said first and said second pump drive heads are configured to move 180 degrees out of phase with respect to each other.

6. The pump as claimed in claim 1 wherein said pump is configured to be coupled to a patient's venous system, and wherein said fluid is blood and said pump is a heart pump providing a pulsatile flow of blood within said patient, wherein said controller is configured to apply said energizing current to said motor in a predetermined waveform based upon said maximum positive energizing current setting established in said controller thereby providing systole blood flow, maximum negative energizing current setting established in said controller thereby providing diastole blood flow, a cycle rate setting established in said controller, and the ratio of systole to diastole blood flow established in said controller such that said pump is configured to provide physiological pulsatile blood flow by ensuring that a maximum volume of blood for a given pressure at a predetermined time and target pressure is displaced within said fluid chamber and within a patient's arterial system.

7. The pump as claimed in claim 1 wherein said pump includes an actuator housing coupled to said deformable fluid housing by way of a tube, said actuator housing defining an actuator chamber having an actuation fluid and a deformable wall proximate said pump drive head, said fluid housing containing said fluid to be pumped and including inlet and outlet ports, wherein said pump drive head deforms said deformable wall of said actuator chamber causing said actuation fluid to flow through said tube and deform said deformable fluid housing, thereby creating a pressure differential within said fluid housing which causes said fluid to be pumped to flow through said inlet and outlet ports.

8. The pump of claim 1 wherein said at least one valve is configured to allow for a slight reversal in the flow of said fluid.

9. The pump of claim 1 wherein said valve is selected from the group consisting of a ball valve, a gate valve, a pinch valve, a magnetic valve, a multi leaflet valve and a butterfly valve.

10. The pump of claim 1 wherein said valve includes a ball valve, and wherein said at least one fluid housing includes at least one port, said port including a ball valve retainer region, a valve seat, and an occluder ball disposed in said ball valve retainer region, wherein said pump drive head is configured to deform said deformable fluid chamber and cause a pressure differential within said fluid chamber thus changing the volume of said fluid chamber and forcing said fluid in or out said fluid chamber, wherein said pressure differential causes said occluder ball to move from a first position within said ball valve retainer region whereby said fluid cannot pass through said port, to a second position within said ball valve retainer region whereby said occluder ball is forced against said valve retainer and said fluid moves annular to and generally around said occluder ball, and wherein said movement of said occluder ball from said first position to said second position creates a slight reversal in the flow of said fluid.

11. The pump as claimed in claim 1 wherein said pump includes first and second linear electromagnetic drive motors and a first and a second fluid housing and a first and a second pump drive head coupled to said first and second linear electromagnetic motors respectively, and wherein said controller is coupled to said first and second linear electromagnetic motors and configured to apply an energizing current to each said first and second linear electromagnetic motors in a predetermined waveform such that said first and said second pump drive heads are caused to move 180 degrees out of phase with respect to each other.

12. The pump as claimed in claim 1 wherein said controller is configured to provide physiological pulsatile flow by ensuring that a maximum volume of fluid for a given pressure at a predetermined time and target pressure is displaced within said fluid chamber and output from said pump.

13. The pump as claimed in claim 1 wherein said controller is configured to provide physiological pulsatile blood flow by ensuring that a maximum volume of blood for a given pressure at a predetermined time and target pressure is displaced within said fluid chamber and within a patient's arterial system.

14. A cardiopulmonary bypass system configured to provide physiological pulsatile blood flow, the system comprising at least a first pump including:
at least a first linear electromagnetic motor;
at least one pump drive head coupled to said at least a first linear electromagnetic motor, said pump drive head configured for moving in a linear direction;
at least a first deformable fluid housing, responsive to said linear movement of said a least one pump drive head, defining a fluid chamber configured to contain blood, said first deformable fluid housing including an inlet and an outlet port configured for allowing said blood to pass generally into and generally out of said fluid housing respectively, each port including a ball valve configured for moving between a first and a second position wherein in said first position said fluid can pass through said port and wherein in said second position said fluid cannot pass through said port, wherein said pump drive head is configured to deform said deformable fluid chamber causing a pressure differential within said deformable fluid chamber which causes said ball valves to move from said first to said second position and creates a slight reversal in the flow of said blood in said deformable fluid chamber, wherein said first pump is configured to pump said blood from a venous reservoir into said input port and into a heat exchanger, an oxygenator and an arterial filter all coupled to said outlet port of said at least a first pump and into a patient's arterial system; and
a controller, coupled to said at least one linear motor, and configured to apply an energizing current to said linear electromagnetic motor in a predetermined waveform based upon a maximum positive energizing current value (systole) setting established in said controller, a maximum negative energizing current value (diastole) setting established in said controller, a cycle rate setting established in said controller, and the ratio of maximum positive to maximum negative energizing current value established in said controller such that said controller is configured to cause said pump to provide physiological pulsatile blood flow by ensuring that a maximum volume of blood for a given pressure at a predetermined time and target pressure is displaced within said fluid chamber and within a patient's arterial system.

15. The cardiopulmonary bypass system as claimed in claim 14 wherein said linear electromagnetic motor includes:
   a core defining an air gap;
   at least one coil disposed around at least a portion of said core proximate said air gap; and
   a magnet member located in said air gap and movable in said linear direction.

16. The cardiopulmonary bypass system as claimed in claim 15 wherein said pump drive head is coupled to said magnet member.

17. The cardiopulmonary bypass system as claimed in claim 14 wherein a first and a second pump drive head are coupled to a first and a second end of said first motor and move 180 degrees out of phase with respect to each other, wherein said first and said second pump heads are configured to cause alternating pressure differentials within first and said second deformable fluid housings of first and said second pumps respectively.

18. The cardiopulmonary bypass system as claimed in claim 14 wherein each of said pumps includes an actuator housing coupled to said deformable fluid housings through a tube, each of said actuator housings defining an actuator chamber having an actuation fluid and a deformable wall proximate said pump drive heads, wherein said pump drive heads are configured to deform said deformable walls of said actuator chambers causing said actuation fluids to flow through said tubes and deform said deformable fluid housings, thereby creating a pressure differential within said deformable fluid housings which causes said blood to be pumped to flow through said inlet and outlet ports.

* * * * *